(12) United States Patent
Rosenblum

(10) Patent No.: US 9,953,307 B2
(45) Date of Patent: Apr. 24, 2018

(54) METHOD OF PAYMENT ASSESSMENT TO CLINICAL STUDY VOLUNTEERS

(75) Inventor: John Rosenblum, Calais, VT (US)

(73) Assignee: ORACLE INTERNATIONAL CORPORATION, Redwood Shores, CA (US)

( * ) Notice: Subject to any disclaimer, the term of this patent is extended or adjusted under 35 U.S.C. 154(b) by 23 days.

(21) Appl. No.: 13/558,474

(22) Filed: Jul. 26, 2012

(65) Prior Publication Data

US 2014/0032229 A1    Jan. 30, 2014

(51) Int. Cl.
*G06Q 50/22* (2012.01)
*G06Q 50/24* (2012.01)
*G06Q 20/22* (2012.01)

(52) U.S. Cl.
CPC ............. *G06Q 20/22* (2013.01); *G06Q 50/22* (2013.01)

(58) Field of Classification Search
CPC ........ G06Q 50/22; G06Q 10/10; G06Q 50/24; G06Q 20/00; G06Q 30/04

USPC ........................................................ 705/2, 3
See application file for complete search history.

(56) References Cited

U.S. PATENT DOCUMENTS

| | | | |
|---|---|---|---|
| 2005/0182664 A1* | 8/2005 | Abraham-Fuchs et al. | 705/3 |
| 2007/0067189 A1* | 3/2007 | Boris et al. | 705/3 |
| 2008/0183498 A1* | 7/2008 | Nichols et al. | 705/2 |
| 2011/0010087 A1* | 1/2011 | Wons et al. | 701/201 |
| 2012/0123789 A1* | 5/2012 | Patel | 705/2 |
| 2013/0317836 A1* | 11/2013 | Wons et al. | 705/2 |

* cited by examiner

*Primary Examiner* — Maroun P Kanaan
(74) *Attorney, Agent, or Firm* — Cooper Legal Group, LLC

(57) ABSTRACT

Systems, methods, and other embodiments associated with generating payments to volunteers in clinical trials are described. In one embodiment, a method includes receiving volunteer data that specifies a clinical event that has been completed by a given volunteer. The example method also includes determining a payment associated with the clinical event. A financial record is generated that records the determined payment. The financial record is transmitted using a web based browser to a financial system to populate at least one field in a financial database table that is used to generate payments to the volunteer.

17 Claims, 5 Drawing Sheets

_US 9,953,307 B2_

METHOD OF PAYMENT ASSESSMENT TO CLINICAL STUDY VOLUNTEERS

BACKGROUND

In clinical trials, groups of volunteers are studied to collect information such as safety data and drug metabolism data. Volunteers are given monetary compensation to compensate them for time spent away from other activities and reimburse their travel expenses. Financial payments are generally based on the completion of clinical events within the clinical study such as attending a screening visit, receiving a dose of the study drug, or for completing the last clinical event.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Records of financial payments are manually processed to provide compensation in a timely manner to volunteers. Upon a volunteer's completion of the clinical events, clinic administrators spend a considerable amount of time calculating and recording compensation. This information is then often hand transcribed into a financial system so that checks can be cut or automatic deposits can be made. It is difficult to provide appropriate user security controls, prevent errors, or pay volunteers in an expedient manner so that payments are available when volunteers complete the study and leave the clinic.

Volunteers typically request immediate payment. Since payments are processed by clinical administrators, there are a number of subsequent steps involved in transferring data acquired at the clinic to the department that oversees the financial side of the operation. Thus, there are a number of subsequent steps to completion of the clinical event before a payment can be processed. The subsequent steps introduce delay and the possibility of error. The process is further resource intensive.

Systems and methods are described herein that provide support for payment assessments associated with clinical trials in the life sciences, pharmaceutical, and medical fields. Specifically, the system communicates and approves financial records generated upon completion of clinical events. Volunteers receive payment based on the corresponding financial record. The system provides a secure user interface that allows a clinic administrator to efficiently assign a compensation method and compensation amount to clinical events.

Payments to a volunteer are calculated when the volunteer data indicates that the volunteer has completed a clinical event for which the volunteer is compensated. The system allows clinic administrator to edit, delete, and add volunteer payments before data is approved. Once the data is approved by the clinic administrator, the data is transferred using a web service to interface with financial system and/or debit card systems. The external financial system records the payments in a clinical financial system. Additionally, the data can be transferred to the debit card system to give volunteers access to cash via debit card accounts or to transfer a cash amount onto a debit card that is given the volunteer at the clinic.

Figure 1:
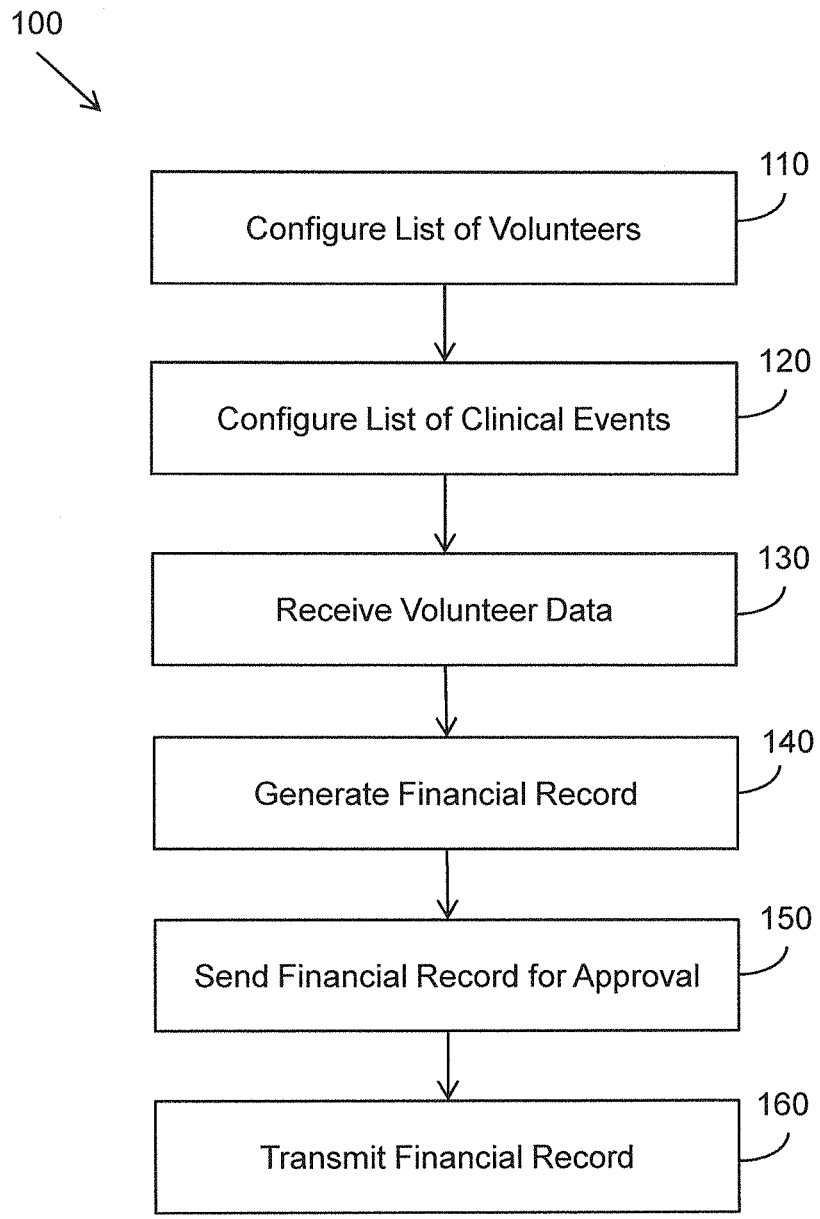
FIG. 1 illustrates one embodiment of a method associated with generating payments to volunteers in clinical trials.

With reference to FIG. 1, one embodiment of a method 100 associated with generating payments to volunteers in clinical trials is illustrated. The method 100 is performed in a web serviced application used for managing clinical studies. Web-based protocol handlers allow web-based applications to operate online. Furthermore, due to the online operation of the functionality of method 100, the functionality occurs in real-time and generates immediate responses.

At 110, a user employs the web service to configure a list of volunteers. The volunteers may be subjects in a clinical study or patients participating in an experimental trial. The volunteers are compensated for their participation based on completing clinical events. At 120, a list of clinical events is configured. The clinical events are based on a chronological protocol that defines milestones (e.g., receiving a dosage, finishing an activity, taking a blood sample) in the study or trial. Respective clinical events are mapped to respective payments. The payments may be flat fees or be variable based on clinical factors (e.g., the invasiveness of a procedure, the amount of time it takes to complete the event, the particular volunteer that completes the event, a number of miles traveled to reach the clinic, and so on).

At 130, volunteer data is received. The volunteer data indicates completion of a clinical event. In response to receiving the volunteer data, a financial record that specifies a payment due by virtue of completion of the clinical event is automatically generated, at 140, in real-time as the clinical study progresses. Authorized clinical administrators can access the financial record to add, edit, or delete the financial record. Additionally, new financial records can be created or associated with the financial record. Any records that have been edited, deleted, or added are saved for reporting.

At 150, the financial record is transmitted to a clinical administrator for approval. The clinical administrator checks the financial record for accuracy. The financial record may be sent to more than one clinical administrator for approval. For example, financial records indicating that a volunteer is to be paid more than a predetermined dollar amount (e.g. $100.00) trigger that second clinical administrator approve the financial record. Alternatively, a financial record including personal information (e.g., a social security number, bank account number, routing number) may be sent to a clinical administrator having a specified security clearance.

Upon approval of the financial record at 150, the financial record is transmitted via the web service to a financial system 160. The financial system may print paper checks or create automatic bank deposits. The financial system also records payments in the clinical organization's financial records. Additionally, the data can be transferred to a debit card system via the web service interface. The debit card system can be used to give volunteers access to debit card accounts that the volunteers are registered to by the clinic organization.

Thus, once volunteer data indicating that a clinical event has been completed, a succession of automated steps takes place based on the clinical event. For example, the financial record is generated based on the completed event which in turn is used to populate financial systems. A web based browser is employed to facilitate communication between clinical systems and financial systems in real time so that payments can be expeditiously issued to volunteers.

Figure 2:
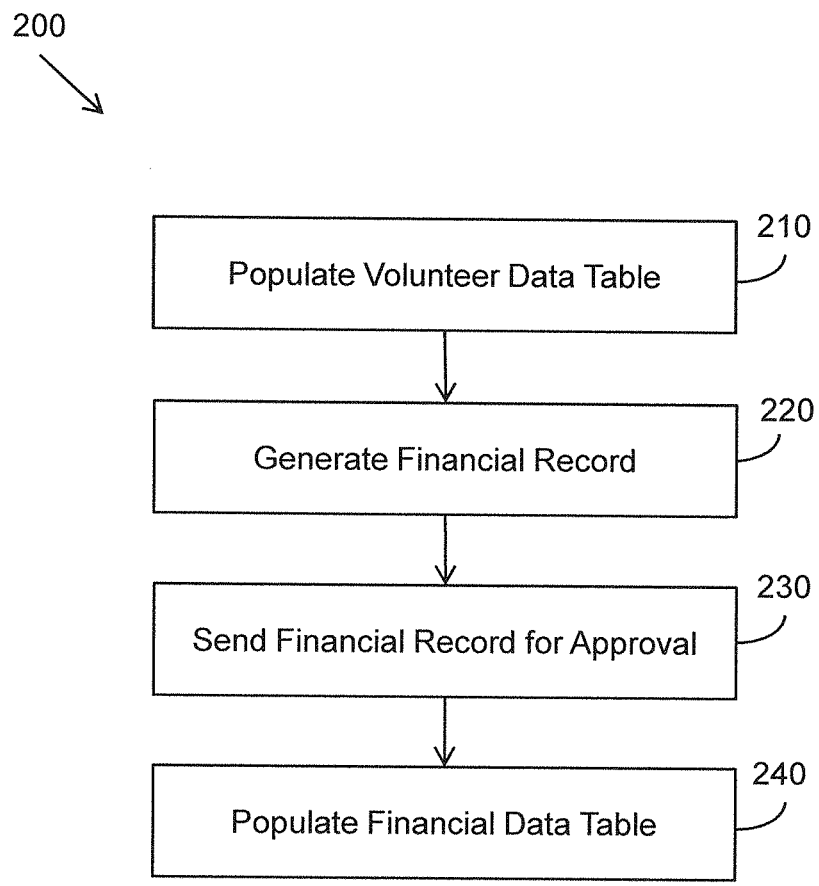
FIG. 2 illustrates another embodiment of a method associated with generating payments to volunteers in clinical trials.

FIG. 2 illustrates one embodiment of a method 200 associated with generating payments to volunteers in clinical trials. In one embodiment the methods described are performed by populating database tables in the clinical system as well as financial systems. Method 200 includes, at 210, populating a volunteer data table. The volunteer data table is populated with data corresponding to completed clinical events. The volunteer data table has a number of data fields configured to receive volunteer data. The data fields may include volunteer data such as a volunteer's name or identifier, gender, weight, blood pressure, or age. The data fields may also indicate the volunteer's progress in the trial, such as particular drugs or treatments a volunteer receives.

At 220, a financial record is generated in response to the volunteer table being populated. To generate the financial record, payment amounts are mapped to the clinical event(s) completed by the volunteer. The mapping is performed by accessing a payment configuration table that records standard payments for clinical events. The financial record is generated automatically.

At 230, the financial record is sent, via a web based browser, to a clinic administrator for approval. The clinical administrator reviews the financial record for accuracy. The clinical administrator may also add, edit, or delete data from the financial record before approving the financial record. For example, the clinic administrator may add data to the financial record regarding additional payments due to the travel that the volunteer incurred to participate in the clinical event. A financial record is not transmitted to the financial system until it is approved. Therefore, changes to a volunteer's trip reimbursement due to, for example, changes to the standard travel reimbursement amount are performed prior to the financial record being approved. Once the financial record is approved by an authorized clinical administrator, the financial record is transmitted, via a web based browser to a financial database.

At 240 a financial data table in the financial database is populated based on the data in the received financial record. The financial data table is automatically populated in response to receiving the financial record. The financial data table may be stored locally in the clinic or remotely in another location. For example, the financial data table may be stored in the same database as the volunteer data table. Alternatively, the financial data table may be stored remotely in an external financial application.

Figure 3:
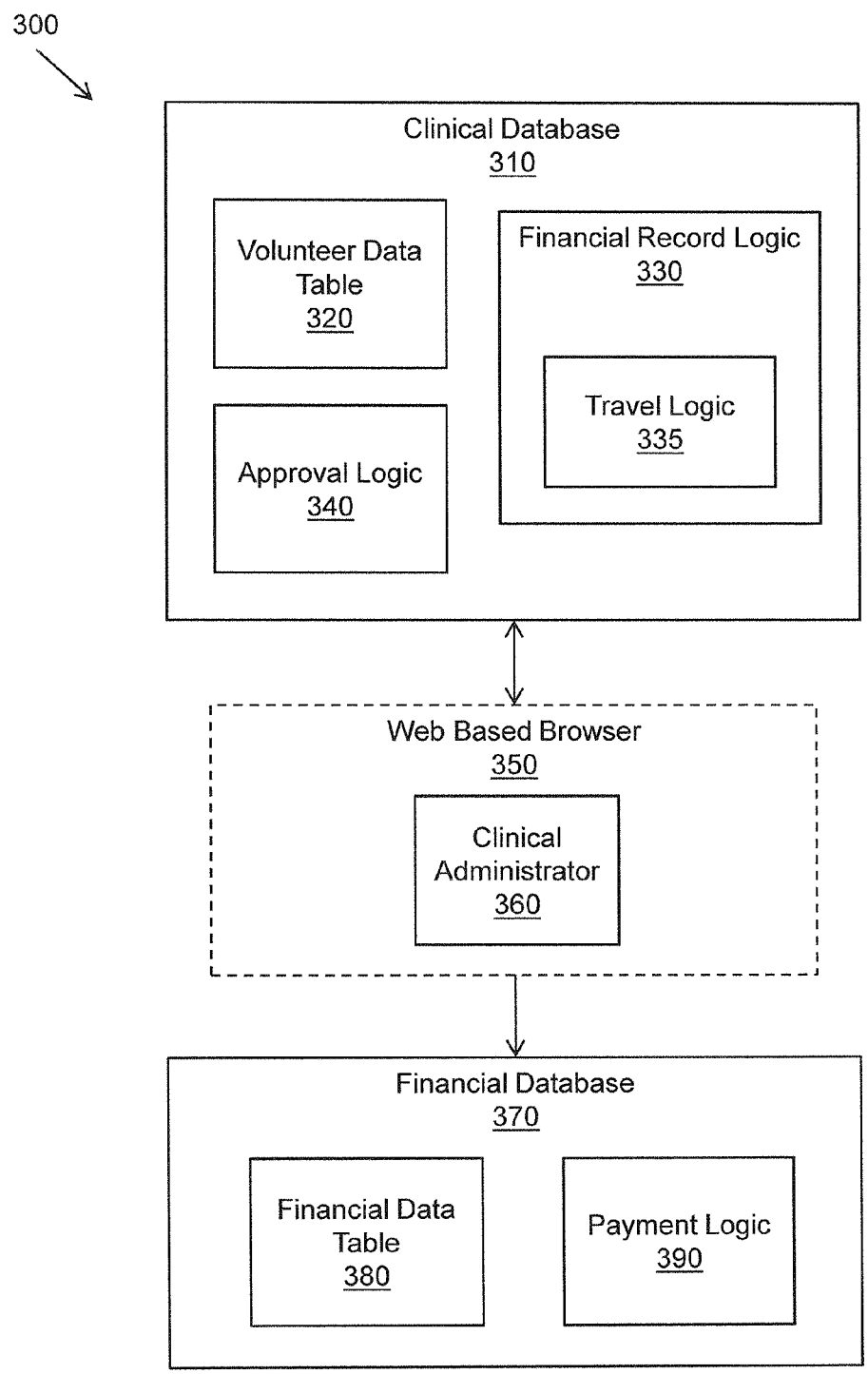
FIG. 3 illustrates one embodiment of a system associated with generating payments to volunteers in clinical trials.

FIG. 3 illustrates one embodiment of a system 300 associated with generating payments to volunteers in clinical trials. The system 300 includes a clinical database 310 having a volunteer data table 320, a financial record logic 330, and an approval logic 340. The clinical database 310 receives volunteer data entered by clinicians (e.g., doctors, nurses, scientists). The volunteer data is stored in the volunteer data table 320. When the volunteer data table 320 is populated, the financial record logic 330 responds by automatically calculating payments due to the volunteer based on stored information about payments. The financial record logic 330 generates a financial record that specifies payments due to volunteers.

There are a number of ways that the financial record logic 330 can be configured to automatically generate a financial record. The financial record logic 330 may receive a signal indicating that volunteer data has been received by the volunteer data table 320 and a financial record is to be generated. Alternatively, the financial record logic 330 may be set up to periodically check the volunteer data table 320 for newly received volunteer data that should result in a financial record being generated. The volunteer data table 320 may be set up to initiate a data push to the financial record logic 330 when volunteer data is received.

The financial record logic 330 includes a travel logic 335. The travel logic 335 has specific values for travel reimbursement for the volunteers and uses this information to automatically calculate travel reimbursements. In one embodiment, the travel logic 335 may access a volunteer's address in the volunteer data table 320 to determine the amount travel a volunteer incurred to travel to and from a clinical event. The travel logic 335 may calculate the travel reimbursement multiplied by a scalar value indicating the number of trips made by the volunteer. The travel logic 335 may associate a travel reimbursement with a specific clinical event or receipt of a consent form. The travel reimbursement is added to the financial record. The financial record logic 330 may also include additional logics to calculate payments to be added to the financial record.

The approval logic 340 transmits the financial record to a clinic administrator 360 over the web based browser 350 for approval. The financial record may require the approval of many or tiered administrators. A secure audit controlled browser web based browser 350 allows clinic administrator 360 to edit, delete, add new, review, and approve volunteer payments. The security for the web based browser 350 includes secure socket layer (SSL) or secure user logon.

The approved financial record is sent to a financial database 370. The financial database 370 has a financial data table 380 and a payment logic 390. The financial data table 380 is automatically populated with data from the financial record once the financial record is approved. The system 300 saves a financial record in the financial database 370. The system 300 provides financial database 370 views which allow external reporting tools to access the data for reporting and exporting purposes. The secure web based browser 350 creates audit records for all user changes. Therefore, the financial data table 380 tracks with the clinical database in real-time by employing the web based browser 350.

The payment logic 390 generates a payment to the volunteer based on the data in the financial data table 380. The payment logic 390 may periodically (e.g., every few seconds) access the financial data table 380 to determine if new payments need to be generated. The payment logic 390 may access a check printing, automatic deposit, or debit system to generate a payment distributed to the volunteer. Accordingly, the volunteer is able to receive payment without the delay of manually entering and re-entering data into multiple systems.

Figure 4:
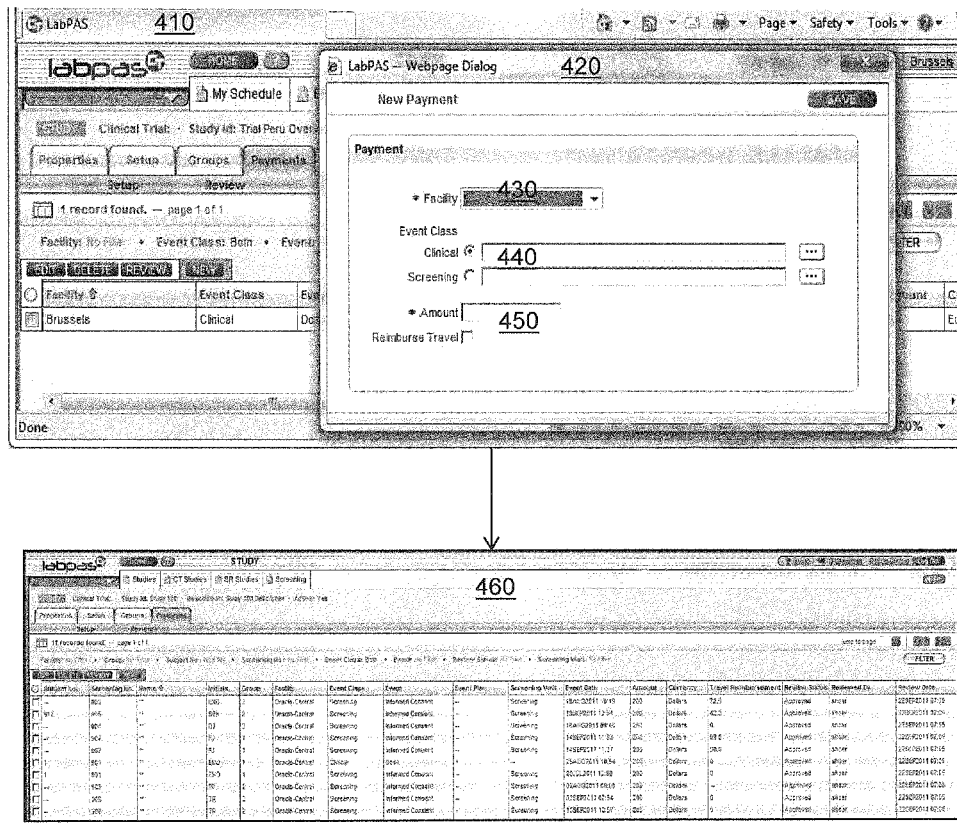
FIG. 4 illustrates an embodiment of a screen shot associated with generating payments to volunteers in clinical trials.

FIG. 4 illustrates a screen shot 410 associated with generating payments to volunteers in clinical trials. The payments setup screen 420 provides clinic administrators with the ability to associate volunteer payments with specific clinical events in a secure user interface which keeps an audit record of all changes. The system provides a web service interface to external financial systems and debit card systems. The payments setup screen 420 has a facility field 430 that is configured to allow a clinician to select a facility. The facility information may be used to calculate travel expenses for volunteers.

An event class field 440 allows a clinician to select whether the event is clinical in nature or a screening procedure. The clinical event is associated with a payment in amount field 450. An example of an event that is clinical in nature is receiving a dosage of a drug. An example of an event that is screening in nature is baseline blood testing. Different payments may be associated with a same type of event, depending on whether it is clinical or screening type.

The system generates volunteer payments and lists them on a Payments Review screen 460 for a clinic administrator to review the data. The Payments Review screen 460 may be accessed by the clinic administrator by way of a web browser. Data can be marked as reviewed or approved. Data records can also be edited and deleted. New data records can be added. An audit record of all changes is kept.

Figure 5:
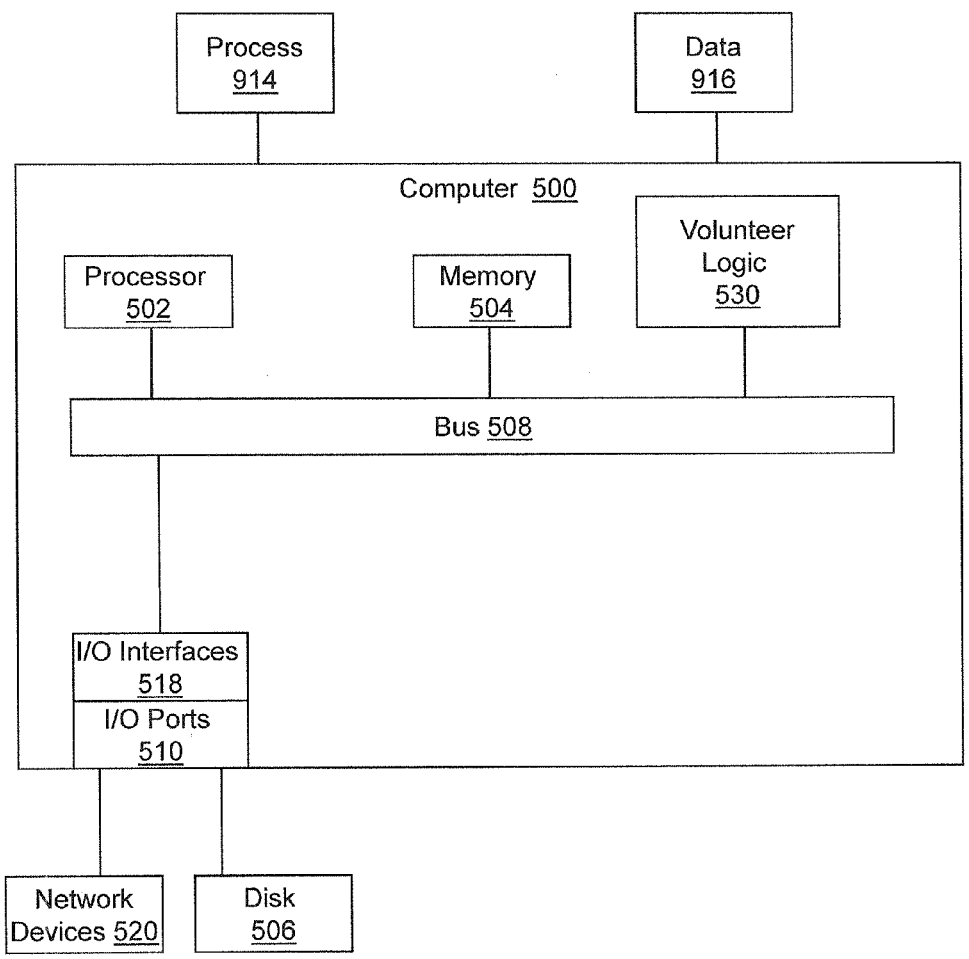
FIG. 5 illustrates an embodiment of a computing system in which example systems and methods, and equivalents, may operate.

FIG. 5 illustrates an example computing device in which example systems and methods described herein, and equivalents, may operate. The example computing device may be a computer 500 that includes a processor 502, a memory 504, and input/output ports 510 operably connected by a bus 508. In one example, the computer 500 may include a volunteer logic 530 configured to assess payments to clinical study volunteers. In different examples, the volunteer logic 530 may be implemented in hardware, a non-transitory computer-readable medium with stored instructions, firmware, and/or combinations thereof. While the volunteer logic 530 is illustrated as a hardware component attached to the bus 508, it is to be appreciated that in one example, the volunteer logic 530 could be implemented in the processor 502.

In one embodiment, volunteer logic 530 is a means (e.g., hardware, non-transitory computer-readable medium, firmware) for generating payments to volunteers in clinical studies. The means may be implemented, for example, as an ASIC programmed to facilitate data editing in a web-based interactive web response system. The means may also be implemented as stored computer executable instructions that are presented to computer 500 as data 516 that are temporarily stored in memory 504 and then executed by processor 502.

Generally describing an example configuration of the computer 500, the processor 502 may be a variety of various processors including dual microprocessor and other multiprocessor architectures. A memory 504 may include volatile memory and/or non-volatile memory. Non-volatile memory may include, for example, ROM, PROM, and so on. Volatile memory may include, for example, RAM, SRAM, DRAM, and so on.

A disk 506 may be operably connected to the computer 500 via, for example, an input/output interface (e.g., card, device) 518 and an input/output port 510. The disk 506 may be, for example, a magnetic disk drive, a solid state disk drive, a floppy disk drive, a tape drive, a Zip drive, a flash memory card, a memory stick, and so on. Furthermore, the disk 506 may be a CD-ROM drive, a CD-R drive, a CD-RW drive, a DVD ROM, and so on. The memory 504 can store a process 514 and/or a data 516, for example. The disk 506 and/or the memory 504 can store an operating system that controls and allocates resources of the computer 500.

The bus 508 may be a single internal bus interconnect architecture and/or other bus or mesh architectures. While a single bus is illustrated, it is to be appreciated that the computer 500 may communicate with various devices, logics, and peripherals using other busses (e.g., PCIE, 1394, USB, Ethernet). The bus 508 can be types including, for example, a memory bus, a memory controller, a peripheral bus, an external bus, a crossbar switch, and/or a local bus.

The computer 500 may interact with input/output devices via the i/o interfaces 518 and the input/output ports 510. Input/output devices may be, for example, a keyboard, a microphone, a pointing and selection device, cameras, video cards, displays, the disk 506, the network devices 520, and so on. The input/output ports 510 may include, for example, serial ports, parallel ports, and USB ports.

The computer 500 can operate in a network environment and thus may be connected to the network devices 520 via the i/o interfaces 518, and/or the i/o ports 510. Through the network devices 520, the computer 500 may interact with a network. Through the network, the computer 500 may be logically connected to remote computers. Networks with which the computer 500 may interact include, but are not limited to, a LAN, a WAN, and other networks.

In another embodiment, the described methods and/or their equivalents may be implemented with computer executable instructions. Thus, in one embodiment, a non-transitory computer-readable medium is configured with stored computer executable instructions that when executed by a machine (e.g., processor, computer, and so on) cause the machine (and/or associated components) to perform the method.

While for purposes of simplicity of explanation, the illustrated methodologies in the figures are shown and described as a series of blocks, it is to be appreciated that the methodologies are not limited by the order of the blocks, as some blocks can occur in different orders and/or concurrently with other blocks from that shown and described. Moreover, less than all the illustrated blocks may be used to implement an example methodology. Blocks may be combined or separated into multiple components. Furthermore, additional and/or alternative methodologies can employ additional blocks that are not illustrated.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

ASIC: application specific integrated circuit.
CD: compact disk.
CD-R: CD recordable.
CD-RW: CD rewriteable.
DVD: digital versatile disk and/or digital video disk.
HTTP: hypertext transfer protocol.
LAN: local area network.
PCI: peripheral component interconnect.
PCIE: PCI express.
RAM: random access memory.
DRAM: dynamic RAM.
SRAM: synchronous RAM.

ROM: read only memory.

PROM: programmable ROM.

EPROM: erasable PROM.

EEPROM: electrically erasable PROM.

SQL: structured query language.

OQL: object query language.

USB: universal serial bus.

XML: extensible markup language.

WAN: wide area network.

"Computer communication", as used herein, refers to a communication between computing devices (e.g., computer, personal digital assistant, cellular telephone) and can be, for example, a network transfer, a file transfer, an applet transfer, an email, an HTTP transfer, and so on. A computer communication can occur across, for example, a wireless system (e.g., IEEE 802.11), an Ethernet system (e.g., IEEE 802.3), a token ring system (e.g., IEEE 802.5), a LAN, a WAN, a point-to-point system, a circuit switching system, a packet switching system, and so on.

"Computer-readable medium", as used herein, refers to a non-transitory medium that stores instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

In some examples, "database" is used to refer to a table. In other examples, "database" may be used to refer to a set of tables. In still other examples, "database" may refer to a set of data stores and methods for accessing and/or manipulating those data stores.

"Data store", as used herein, refers to a physical and/or logical entity that can store data on a non-transitory computer readable medium. A data store may be, for example, a database, a table, a file, a list, a queue, a heap, a memory, a register, and so on. In different examples, a data store may reside in one logical and/or physical entity and/or may be distributed between two or more logical and/or physical entities.

"Logic", as used herein, includes but is not limited to hardware, firmware, a non-transitory computer readable medium that stores instructions, instructions in execution on a machine, and/or combinations of each to perform a function(s) or an action(s), and/or to cause a function or action from another logic, method, and/or system. Logic may include a microprocessor controlled by an algorithm, a discrete logic (e.g., ASIC), an analog circuit, a digital circuit, a programmed logic device, a memory device containing instructions, and so on. Logic may include one or more gates, combinations of gates, or other circuit components. Where multiple logics are described, it may be possible to incorporate the multiple logics into one physical logic. Similarly, where a single logic is described, it may be possible to distribute that single logic between multiple physical logics.

"User", as used herein, includes but is not limited to one or more persons, computers or other devices, or combinations of these.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the disclosure is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is used in the detailed description or claims (e.g., A or B) it is intended to mean "A or B or both". When the applicants intend to indicate "only A or B but not both" then the phrase "only A or B but not both" will be used. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is used herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be used.

What is claimed is:

1. A non-transitory computer-readable medium storing computer-executable instructions that when executed by a computer including a processor cause the computer to:

in response to receiving volunteer data entered by a clinician that specifies a clinical event that has been completed by a given volunteer at a clinical event location, populate a volunteer data table with the volunteer data, where the volunteer data table is configured to automatically, when new data populates the volunteer data table, push at least a portion of the volunteer data to a financial record logic executed by the processor of the computer;

in response to the push of the volunteer data, access, with the financial record logic, a configuration table that maps clinical events to respective payment amounts to determine an amount of a payment associated with the clinical event;

generate, with the financial record logic, a financial record that records the determined amount of the payment and selected portions of the volunteer data;

in response to completion of a new financial record, render a payment screen that lists unpaid financial records including the new financial record for access by a clinic administrator, where the payment screen provides an interface through which the clinic administrator can modify or approve the determined amount of payment in the financial records on the payment screen, where the rendering of the payment screen that includes the new financial record results, without human interaction, automatically from receiving the volunteer data such that delay between the clinical event and the rendering of the screen is negligible;

in response to receiving approval of the financial record by the clinic administrator, transmit the financial record using a web based browser to a financial system to automatically populate a financial database table that allows an external reporting tool to access data populated within the financial database table for reporting and exporting;

use a payment logic executed by the processor of the computer to periodically access the financial database table to determine whether a new payment is to be generated based upon population of new data within the financial database table; and in response to determining that the new payment is to be generated based upon the automatic population of the financial database table using the payment logic, automatically interact, using at least one processor, with a payment system to i) print a check payable to the volunteer by a printer or ii) credit a debit card controlled by the volunteer for the determined amount of payment approved by the clinic administrator, such that the check or debit card credit can be immediately issued, in tangible form, to the given volunteer, where the issuing of the check or debit card results, without human interaction, automatically from receiving approval from the clinic administrator, such that delay between receiving approval and the issuing of the payment is negligible.

2. The non-transitory computer-readable medium of claim 1, the computer-executable instructions further causing the computer to configure a list of volunteers participating in the clinical trial with volunteer data including one or more of a volunteer identifier, volunteer home address, weight, gender, previous medical conditions, and age.

3. The non-transitory computer-readable medium of claim 1, the computer-executable instructions further causing the computer to, when a clinical event corresponding to a trip to or from a clinic occurs, generate a travel expense payment by calculating a travel reimbursement to be paid to the volunteer using a home address of the volunteer.

4. The non-transitory computer-readable medium of claim 1, where the payment is issued to the volunteer before the volunteer leaves the clinical event location.

5. The non-transitory computer-readable medium of claim 1, where the payment is issued to the volunteer as a check before the volunteer leaves the clinical event location.

6. The non-transitory computer-readable medium of claim 1, the computer-executable instructions further causing the computer to:
determine clinical factors corresponding to the clinical event completed by the volunteer, the clinical factors comprising:
i) an invasiveness of a procedure,
ii) an amount of time to complete the clinical event,
iii) information about the volunteer, and
iv) a distance traveled by the volunteer to reach the clinical event location;
and
determine the amount of payment associated with the clinical event based upon the clinical factors.

7. The non-transitory computer-readable medium of claim 1, the computer-executable instructions further causing the computer to:
determine one or more clinical factors, comprising an invasiveness of a procedure, corresponding to the clinical event completed by the volunteer; and
determine the amount of payment associated with the clinical event based upon the one or more clinical factors.

8. The non-transitory computer-readable medium of claim 1, the computer-executable instructions further causing the computer to:
determine one or more clinical factors comprising an amount of time to complete the clinical event; and
determine the amount of payment associated with the clinical event based upon the one or more clinical factors.

9. The non-transitory computer-readable medium of claim 1, the computer-executable instructions further causing the computer to:
determine one or more clinical factors comprising information about the volunteer; and
determine the amount of payment associated with the clinical event based upon the one or more clinical factors.

10. The non-transitory computer-readable medium of claim 1, the computer-executable instructions further causing the computer to:
determine one or more clinical factors comprising a distance traveled by the volunteer to reach the clinical event location; and
determine the amount of payment associated with the clinical event based upon the one or more clinical factors.

11. A computing system, comprising:
a processor configured to receive volunteer data entered by a clinician that specifies a clinical event that has been completed by a given volunteer at a clinical event location;
a volunteer data table configured to: i) receive the volunteer data, and ii) initiate a push of at least a portion of the volunteer data to a financial record logic;
the financial record logic, where the financial record logic is configured to, in response to the push of volunteer data, cause the processor to:
access a configuration table that maps payment amounts to respective clinical events; and
generate a financial record that records a payment amount associated with the clinical event and selected portions of the volunteer data;
and
in response to receiving authorization of the financial record, utilize a web based browser to transmit the financial record to a financial system;
a financial data table located in the financial system having at least one field configured to be populated based, at least in part, on the financial record;
approval logic configured to cause the processor to, in response to completion of a new financial record:
render a payment screen that lists unpaid financial records including then new financial record for access by a clinic administrator, where the payment screen provides an interface through which the clinic administrator can modify or approve the determined amount of payment in the financial records on the payment screen;
where the rendering of the payment screen that includes the new financial record results, without human interaction, automatically from receiving the volunteer data such that delay between the clinical even and the rendering of the screen is negligible;
in response to receiving approval of the financial record by the clinic administrator, transmitting the financial record using a web based browser to the financial system to automatically populate the financial data table, the financial data table allowing an external reporting tool to access data populated within the financial database table for reporting and exporting; and a payment logic configured to, in response to determining that a new payment is to be generated based upon the automatic population of the financial data table, automatically cause the processor to interact with a payment system to i) print a check, by a printer, payable to the volunteer or ii) credit a debit card controlled by the volunteer for the determined amount of payment approved by the clinic administrator, such that the check or debit card credit can be immediately issued, in tangible form, to the given volunteer;

where the issuing of the check or debit card results, without human interaction, automatically from receiving approval from the clinic administrator, such that delay between receiving approval and the issuing of the payment is negligible.

12. The computing system of claim 11, further comprising an approval logic configured to transmit the financial record using the web based browser to at least one clinical administrator for approval.

13. The computing system of claim 12, where the approval logic is configured to transmit the financial record to the at least one clinical administrator based, at least in part, on personal information contained in the financial record.

14. The computing system of claim 11, further comprising a travel logic configured to calculate the amount of a payment to the volunteer corresponding to travel expenses incurred by the volunteer.

15. The computing system of claim 14, where the travel logic is configured to determine a distance from a location where the clinical event occurred to a home address of the volunteer.

16. A computer-implemented method comprising:

receiving volunteer data entered by a clinician that specifies a clinical event that has been completed by a given volunteer at a clinical event location;

populating a volunteer data table with the volunteer data, where the volunteer data table is configured to automatically, when new data populates the volunteer data table, push at least a portion of the volunteer data to a financial record logic;

in response to the push of the volunteer data, accessing, with the financial record logic, a configuration table that maps clinical events to respective payment amounts to determine an amount of a payment associated with the clinical event;

generating, with the financial record logic, a financial record that records the determined amount of the payment and selected portions of the volunteer data;

in response to completion of a new financial record, rendering a payment screen that lists unpaid financial records including the new financial record for access by a clinic administrator, where the payment screen provides an interface through which the clinic administrator can modify or approve the determined amount of payment in the financial records on the payment screen, where the rendering of the payment screen that includes the new financial record results, without human interaction, automatically from receiving the volunteer data such that delay between the clinical event and the rendering of the screen is negligible;

in response to receiving authorization of the financial record by the clinic administrator, transmitting the financial record using a web based browser to a financial system to automatically populate a financial database table; and in response to determining that a new payment is to be generated based upon the automatic population of the financial database table, automatically interacting with a payment system to i) print a check, by a printer, payable to the volunteer or ii) credit a debit card controlled by the volunteer for the determined amount of payment approved by the clinic administrator, such that the check or debit card credit can be immediately issued, in tangible form, to the given volunteer, where the issuing of the check or debit card results, without human interaction, automatically from receiving approval from the clinic administrator, such that delay between receiving approval and the issuing of the payment is negligible.

17. The computer-implemented method of claim 16, further comprising, when a clinical event corresponding to a trip to or from a clinic occurs, generating, by the computer, a travel expense payment by calculating a travel reimbursement to be paid to the volunteer using a home address of the volunteer.

* * * * *

UNITED STATES PATENT AND TRADEMARK OFFICE
CERTIFICATE OF CORRECTION

PATENT NO. : 9,953,307 B2
APPLICATION NO. : 13/558474
DATED : April 24, 2018
INVENTOR(S) : Rosenblum Page 1 of 1

It is certified that error appears in the above-identified patent and that said Letters Patent is hereby corrected as shown below:

In the Claims

In Column 10, Line 55, in Claim 11, delete "then" and insert -- the --, therefor.

In Column 10, Line 64, in Claim 11, delete "even" and insert -- event --, therefor.

Signed and Sealed this
Sixth Day of November, 2018

Andrei Iancu
*Director of the United States Patent and Trademark Office*